United States Patent
Johnson et al.

(10) Patent No.: US 6,682,532 B2
(45) Date of Patent: Jan. 27, 2004

(54) COUPLING SYSTEM AND METHOD FOR EXTENDING SPINAL INSTRUMENTATION

(75) Inventors: Robert G. Johnson, San Antonio, TX (US); Richard C. Techiera, New Bedford, MA (US)

(73) Assignee: DePuy Acromed, Inc., Raynham, MA (US)

( * ) Notice: Subject to any disclaimer, the term of this patent is extended or adjusted under 35 U.S.C. 154(b) by 0 days.

(21) Appl. No.: 10/105,109

(22) Filed: Mar. 22, 2002

(65) Prior Publication Data

US 2003/0181914 A1 Sep. 25, 2003

(51) Int. Cl.[7] .......................... A61B 17/56; A61B 17/58; A61F 2/30
(52) U.S. Cl. ............................................. 606/73; 606/61
(58) Field of Search .............................. 606/61, 69, 70, 606/71, 72, 73

(56) References Cited

U.S. PATENT DOCUMENTS

| | | | |
|---|---|---|---|
| 4,611,581 A | | 9/1986 | Steffee |
| 4,696,290 A | | 9/1987 | Steffee |
| 5,102,412 A | | 4/1992 | Rogozinski |
| 5,127,912 A | | 7/1992 | Ray et al. |
| 5,242,446 A | | 9/1993 | Steffee et al. |
| 5,261,911 A | | 11/1993 | Carl |
| 5,300,073 A | | 4/1994 | Ray et al. |
| 5,334,203 A | | 8/1994 | Wagner |
| 5,397,363 A | | 3/1995 | Gelbard |
| 5,470,333 A | * | 11/1995 | Ray .............................. 606/61 |
| 5,474,551 A | | 12/1995 | Finn et al. |
| 5,498,262 A | * | 3/1996 | Bryan .......................... 606/61 |
| 5,507,745 A | | 4/1996 | Logroscino et al. |
| 5,545,167 A | | 8/1996 | Lin |
| 5,613,968 A | * | 3/1997 | Lin .............................. 606/61 |
| 5,693,053 A | | 12/1997 | Estes |
| 5,766,254 A | | 6/1998 | Gelbard |
| 5,810,816 A | | 9/1998 | Roussouly et al. |
| 6,080,156 A | | 6/2000 | Asher et al. |
| 6,146,384 A | | 11/2000 | Lee et al. |
| 6,197,028 B1 | | 3/2001 | Ray et al. |
| 6,302,883 B1 | * | 10/2001 | Bono ........................... 606/69 |
| 6,416,515 B1 | * | 7/2002 | Wagner ....................... 606/61 |
| 2003/0036759 A1 | * | 2/2003 | Musso ......................... 606/69 |

OTHER PUBLICATIONS

T. Glenn Pait, MD., et al. "Inside–outside technique for posterior occipitocervical spine instrumentation and stabilization: preliminary results", *J. Neurosurg: Spine*/vol. 90(1–7) Jan., 1999.

* cited by examiner

Primary Examiner—Eduardo C. Robert
Assistant Examiner—Anuradha Ramana
(74) Attorney, Agent, or Firm—Nutter, McClennen & Fish, LLP

(57) ABSTRACT

A coupler for connecting a first, slotted, implanted spinal fixation element to a second spinal fixation element includes a post and a head disposed on a distal end of the post. The head of the coupler has a width shorter than a width of a slot in the first, slotted, implanted spinal fixation element, and a length longer than the width of the slot in the first, slotted, implanted spinal fixation element. The coupler with a head so configured can be placed in a first orientation so that the head passes through the slot in the first, slotted, implanted spinal fixation element, and then can be placed in a second orientation wherein the head is trapped beneath the first, slotted, implanted spinal fixation element while the post having a connecting element extends through the slot. Systems and methods for extending a first, implanted spinal fixation element to one or more additional vertebrae while leaving the first, implanted spinal fixation element in place are also disclosed.

22 Claims, 4 Drawing Sheets

COUPLING SYSTEM AND METHOD FOR EXTENDING SPINAL INSTRUMENTATION

FIELD OF THE INVENTION

The present invention relates to devices, systems and methods that aid in the performance of spinal revision surgery in which previously implanted spinal fixation instrumentation is extended to additional vertebrae. More particularly, the invention provides coupling systems and methods that allow for a first, implanted spinal fixation element to be coupled to a second spinal fixation element while leaving the first element in place.

BACKGROUND OF THE INVENTION

The use of spinal fixation instrumentation to align and/or fix a desired relationship between adjacent vertebral bodies is well established. Such instrumentation typically includes a spinal fixation element, such as a relatively rigid plate or a rod, that is coupled to adjacent vertebrae by attaching the element to pedicle screws which have been inserted into the patient's vertebrae. Once installed, the spinal fixation instrumentation holds the vertebrae in a desired spatial relationship, either until desired healing or spinal fusion has taken place, or for some longer period of time.

While use of such spinal fixation instrumentation is effective in treating a number of spinal disorders and traumas, it sometimes becomes necessary to extend the instrumentation from the vertebrae being treated to one or more additional adjacent vertebrae. This can be accomplished by removing the existing spinal fixation element (in particular, removing the rod(s) or plate(s) that fix the alignment of the previously treated vertebrae), and replacing it with a new element configured to treat all of the vertebrae needing treatment. Spinal fixation elements, however, are carefully shaped and placed to result in a desired alignment. Accordingly, removal, or even sometimes movement, of a spinal fixation element can result in significant effort by a surgeon to realign the previously aligned vertebrae and instrumentation, in addition to treating additional vertebrae. In addition, it is preferable not to remove implanted pedicle screws as the replacement of such screws in the patient's vertebrae can result in the removal of additional bone material from the patient's spine.

Accordingly, there is a need for a coupling system and method for extending previously implanted spinal instrumentation to additional vertebrae without removing the existing instrumentation. In particular, coupling systems and methods that can couple a second spinal fixation element to a first, implanted spinal fixation element while leaving the first element in place would simplify revision surgery for the surgeon, and likely provide many benefits for the patient as well.

SUMMARY OF THE INVENTION

The present invention solves the described problems in the art and others by providing a coupler for connecting a first, slotted, implanted spinal fixation element to a second spinal fixation element. In a first aspect, the invention includes a coupler having a post and a head disposed on a distal end of the post. The head of the coupler has a width shorter than a width of a slot in the first, slotted, implanted spinal fixation element, and a length longer than the width of the slot in the first, slotted, implanted spinal fixation element. The coupler with a head so configured can be placed in a first orientation so that the head passes through the slot in the first, slotted, implanted spinal fixation element, and then can be placed in a second orientation wherein the head is trapped beneath the first, slotted, implanted spinal fixation element while the post having a connecting element extends through the slot. In this way, a coupler can be provided for connecting a second spinal fixation element without removing the first, slotted, implanted spinal fixation element.

In a further aspect of the invention, a system for extending a first, implanted spinal fixation element to one or more additional adjacent vertebrae while leaving the first, implanted spinal fixation element in place is provided. The system includes a second spinal fixation element, a coupler, and a second spinal fixation element attachment member. The coupler has a connecting member and a head disposed on a distal end of the connecting member for holding the coupler to the first, implanted spinal fixation element. The second spinal fixation element attachment member has a coupler attaching portion for attaching to the connecting member of the coupler and a second spinal fixation element attaching portion. In this system, when the coupler is assembled to the first, implanted spinal fixation element, the second spinal fixation element attachment member is assembled to the coupler, and the second spinal fixation element is assembled to the second spinal fixation element; the system extends spinal treatment from the first, implanted spinal fixation element to one or more adjacent vertebrae while leaving the first, implanted spinal fixation element in place.

In one embodiment of this aspect of the invention, the first, implanted spinal fixation element is slotted and the head of the coupler is configured to hold the coupler to a slot on the first, implanted spinal fixation element. In this embodiment, the head has a width shorter than a width of the slot in the first, implanted spinal fixation element, and a length longer than the width of the slot in the first, implanted spinal fixation element. When this coupler is placed in a first orientation, the head passes through the slot, and when the coupler is then placed in a second orientation, the head is trapped beneath the first, implanted spinal fixation element while the connecting member extends through the slot.

In a further embodiment of this aspect of the invention, the second spinal fixation element can be a spinal fixation rod and the second spinal fixation element attaching portion of the second spinal fixation element attachment member can define a bore for accepting and attaching the spinal fixation rod.

In a further aspect of the invention, a method is provided for extending a first, implanted spinal fixation element to one or more additional adjacent vertebrae while leaving the first, implanted spinal fixation element in place. The method includes assembling a coupler having a connecting member and a head disposed on a distal end of the connecting member for holding the coupler to the first, implanted spinal fixation element; assembling a second spinal fixation element attachment member having a coupler attaching portion for attaching to the connecting member of the coupler and a second spinal fixation element attaching portion to the coupler; assembling a second spinal fixation element to the second spinal fixation element attachment member; and fixing the second spinal fixation element to the one or more additional adjacent vertebrae. Each of the steps in this method can be performed while the first, implanted spinal fixation element is left in place.

In one embodiment of this aspect of the invention, the first, implanted spinal fixation element is slotted and the head of the coupler is configured to hold the coupler to a slot on the first, implanted spinal fixation element. The head has a width shorter than a width of the slot in the first, implanted spinal fixation element, and a length longer than the width of the slot in the first, implanted spinal fixation element. The step of assembling the coupler to the first, implanted spinal fixation element can thus include placing the coupler in a first orientation wherein the head passes through the slot, passing the head through the slot, and placing the coupler in a second orientation wherein the head is trapped beneath the first, implanted spinal fixation element while the connecting member extends through the slot.

In a further embodiment of this aspect of the invention, the second spinal fixation element is a spinal fixation rod and the second spinal fixation element attaching portion of the second spinal fixation element attachment member defines a bore for accepting and attaching the spinal fixation rod. In this embodiment, the step of assembling the second spinal fixation element to the to the second spinal fixation element attachment member includes fixing the rod within the bore.

BRIEF DESCRIPTION OF THE DRAWINGS

The invention will be more fully understood from the following detailed description taken in conjunction with the accompanying drawings.

DETAILED DESCRIPTION OF THE INVENTION

Figure 1:
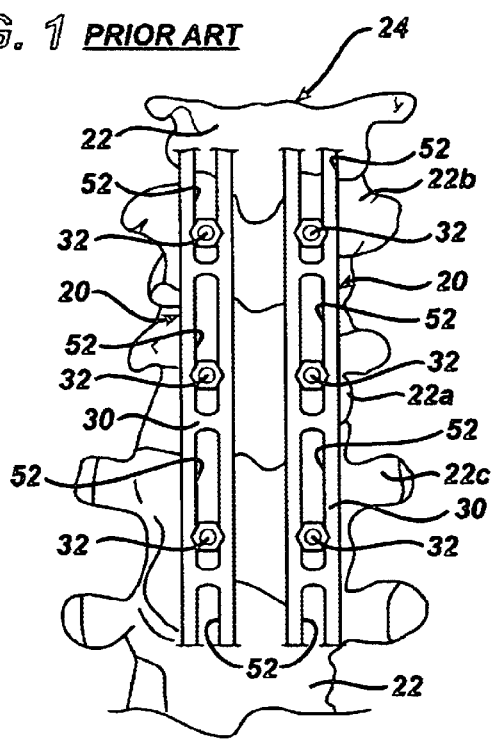
FIG. 1 illustrates exemplary implanted spinal fixation instrumentation known in the art with which the invention may be used.

The present invention provides systems and methods useful for coupling a first, implanted spinal fixation element to a second spinal fixation element so that existing spinal fixation treatment may be extended to additional adjacent vertebrae without removing the implanted spinal fixation element. A pair of common spinal fixation elements 30, slotted plates in this embodiment, are illustrated as implanted to a patient's spine 24 in FIG. 1. Illustrated spinal fixation elements 30 (one spinal fixation element 30 is further illustrated in FIG. 2) are coupled to several vertebrae 22 (specifically, to vertebrae 22c, 22a, and 22b in descending order in FIG. 1) by spinal coupling assemblies 32 (illustrated in further detail in FIG. 3).

Figure 2:
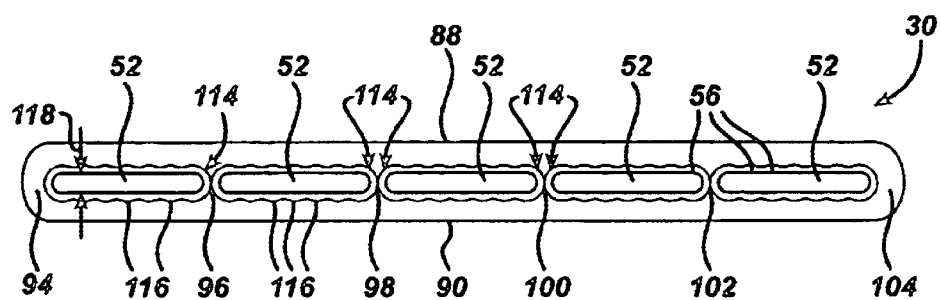
FIG. 2 illustrates a spinal fixation element used in the instrumentation of FIG. 1.

Exemplary spinal plates 30 (FIGS. 1 and 2; and further described in U.S. Pat. No. 4,611,581 to Steffee which is hereby incorporated by reference) include slots 52 through which spinal coupling assemblies 32 may extend. Spinal plates 30 generally include a pair of parallel longitudinally (in the direction of the spine when the plates are implanted) extending beam sections 88, 90 which are interconnected by a plurality of cross sections 94, 96, 98, 100, 102, and 104. The cross sections 94–104 cooperate with beam sections 88, 90 to define slots 52 having a width 118. Slots 52 can include beveled edge portion 114 and can also include a plurality of scallops or recesses 116.

Figure 3:
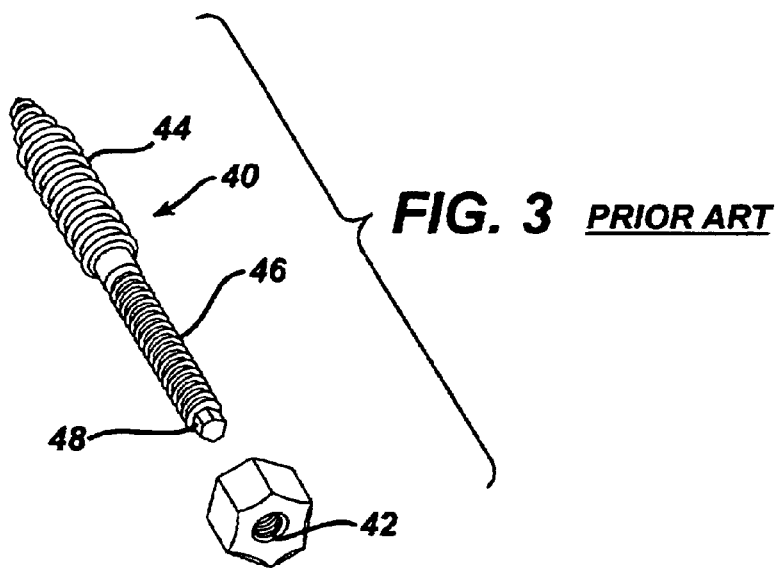
FIG. 3 illustrates a bone coupling element used in the instrumentation of FIG. 1.

Exemplary spinal coupling assembly 32 (FIGS. 1 and 3; also further described in U.S. Pat. No. 4,611,581 to Steffee which is incorporated by reference above) includes a bone coupling element 40 and a nut 42. Bone coupling element 40 includes a distal bone engaging thread 44 which is configured to hold the coupling element to a vertebral body. Bone coupling element 40 also includes a proximal threaded region 46 configured to be threadedly engaged to nut 42. Bone coupling element 40 can also include a proximal driving element 48.

In use, a series of holes are formed in adjacent vertebrae, each hole being narrower in width than the distal threads 44 on bone coupling element 40, and a bone coupling element is screwed into each of the holes to fix the bone coupling elements to the vertebrae while leaving proximal thread 46 extending outside the bone. Spinal fixation element 30 is shaped as desired and placed so that extending proximal threads 46 of the implanted bone coupling elements 40 pass through slots 52, and nuts 42 are screwed onto proximal threads 46 to hold spinal fixation element 30 to the vertebrae. In one embodiment, a side of nut 42 facing spinal fixation element 30 is tapered so as to cooperate with scallops 116 on the spinal fixation element so that, upon tightening, nuts 42 can also fix the spinal fixation element or elements in a longitudinal direction.

Figure 4:
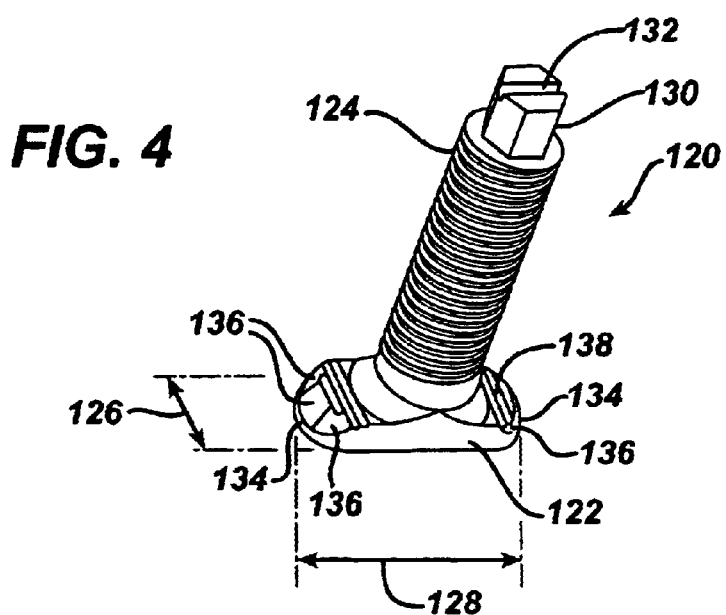
FIG. 4 illustrates a T-coupler of the invention.
Figure 5:
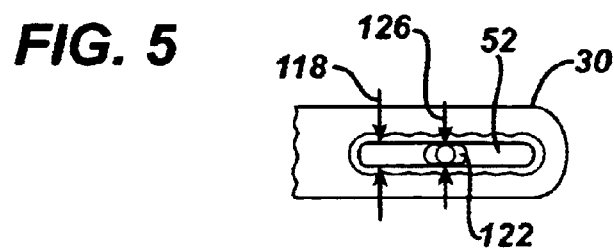
FIG. 5 illustrates the T-coupler of FIG. 4 interacting with the spinal fixation element of FIG. 2 in a first orientation.
Figure 6:
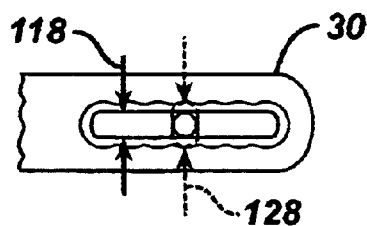
FIG. 6 illustrates the T-coupler of FIG. 4 interacting with the spinal fixation element of FIG. 2 in a second orientation.

A coupling element 120 of the invention, sometimes referred to herein as a "T-coupler" because of the shape of the illustrative embodiment, for coupling an implanted spinal fixation element such as spinal fixation element 30 (illustrated as implanted in FIG. 1) to a second spinal fixation element is illustrated in FIG. 4. T-coupler 120 has a head 122 and post 124. Head 122 is shaped so as to fit through a slot in an implanted spinal fixation element, such as slot 52 in spinal fixation element 30, so that head 122 can pass through slot 52 in a first orientation (illustrated in FIG. 5), but does not pass through when head 122 is placed in a second orientation (illustrated in FIG. 6). In the illustrated embodiment, head 122 has a width 126 that is smaller than width 118 of slot 52, allowing the head to pass through when the head is aligned so that head width 126 fits through slot width 118. Head 122 also has a length 128 that is larger than slot width 118 so that when the head is oriented so that its length is aligned with slot width 118, the head does not pass through the slot.

In use, head 122 is appropriately oriented and passed through the slot of an implanted fixation element (FIG. 5), then rotated approximately 90° so that head 122 is trapped beneath the spinal fixation element (between the spinal fixation element and the spine) while post 124 of T-coupler 120 extends outward from the spinal fixation element. A driving element 130, in this embodiment a hex-head, can be provided on post 124 for orienting T-coupler 120 after passing head 122 though slot 52, and a visual indicator 132 (a groove in the illustrated embodiment) can also be provided so that a surgeon or other operator can readily determine the orientation of head 122.

Illustrated head 122 of T-coupler 120 includes several additional features to facilitate its use as described above.

Both ends 134 of head 122 can have a full radius at their edges to facilitate rotational orientation of the head, and one or more bevels 136 can also be provided proximate to each end 134. V-grooves 138 or other surface features can be provided on the "top" surface of head 122 (the surface that will abut the back of the implanted spinal fixation member) to encourage head 122 to remain in a fixed position with respect to the implanted spinal fixation member upon tightening of T-coupler to the fixation element.

Figure 7:
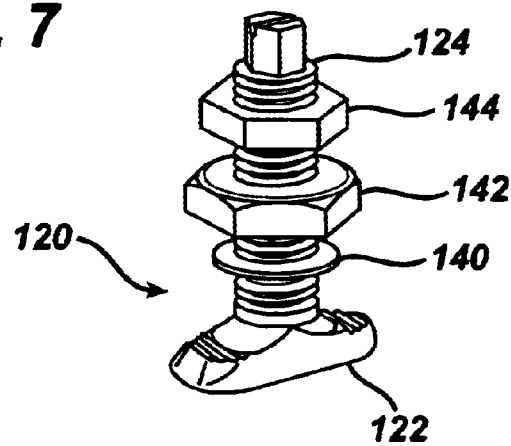
FIG. 7 illustrates the T-coupler of FIG. 4 with fixation hardware.

T-coupler 120 is illustrated in FIG. 7 with hardware appropriate for using the T-coupler to fix a first spinal fixation element to a second spinal fixation element coupler. T-coupler 120 is provided in this embodiment with a conical washer 140, a T-coupler fixing nut 142, and a second spinal fixation element coupler fixing nut 144. After placement and orientation of T-coupler 120 with respect to spinal fixation element 30, washer 140, which can be tapered to cooperate with scallops 116, is placed over post 124, followed by T-coupler fixing nut 142 which can be threadedly engaged with post 124 and tightened to fix T-coupler 120 to fixation element 30. In one embodiment, post 124 can be sized and threaded similarly to proximal threaded region 46 of bone coupling element 40 so that the same hardware and instrumentation (such as, for example, the washers, nuts, and hex drivers) used with the existing or to-be-installed spinal fixation instrumentation can also be used with T-coupler 120.

In the embodiment illustrated in FIGS. 4 and 7, T-coupler 120 head 122 can have a length 128 of approximately 12 millimeters, a width 126 less than approximately 5 millimeters (such as between approximately 4.83 and 4.98 millimeters), and a height of approximately 2 millimeters, while post 124 can have a major diameter approximately equal to the head width 126, and a threaded length of approximately 17 millimeters with a driving element 130 height of approximately 3.18 millimeters for a total overall T-coupler height of approximately 22.18 millimeters. A person of ordinary skill in the art will recognize that these illustrative dimensions can be varied within the spirit of the invention, however, the height of T-coupler 120 head 122 must be kept sufficiently small to fit between the implanted spinal fixation device and a patient's vertebral body in order to be effective as described. All of the illustrated hardware can be formed from materials known in the art to be inert when implanted in the body and having sufficient strength to perform the desired fixation such as stainless steel, titanium, and alloys thereof.

Figure 8:
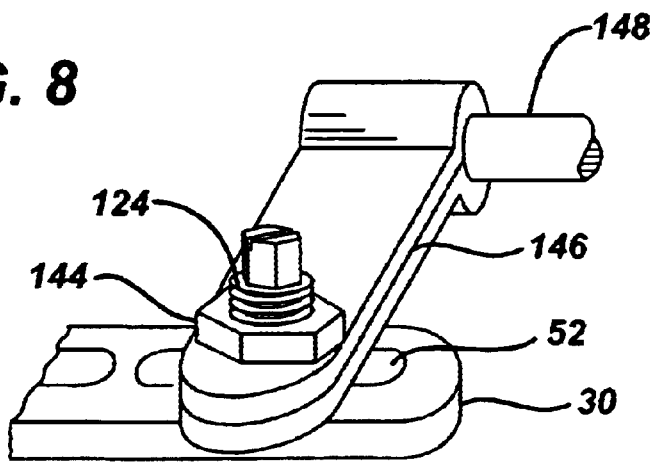
FIG. 8 illustrates a system of the invention for fixing a first implanted spinal fixation element to a second spinal fixation element.

T-coupler 120 is used to fix a first spinal fixation element 30 to a second spinal fixation element 148 in FIG. 8. T-coupler 120 is fixed to spinal fixation element 30 as described above leaving post 124 of the T-coupler extending upward after placement and tightening of washer 140 and nut 142. A second spinal fixation coupling element 146 is then placed over post 124 and fixed with nut 144. A second spinal fixation element 148 is coupled to the second spinal fixation coupling element, typically though not necessarily before tightening nut 144.

Figure 9:
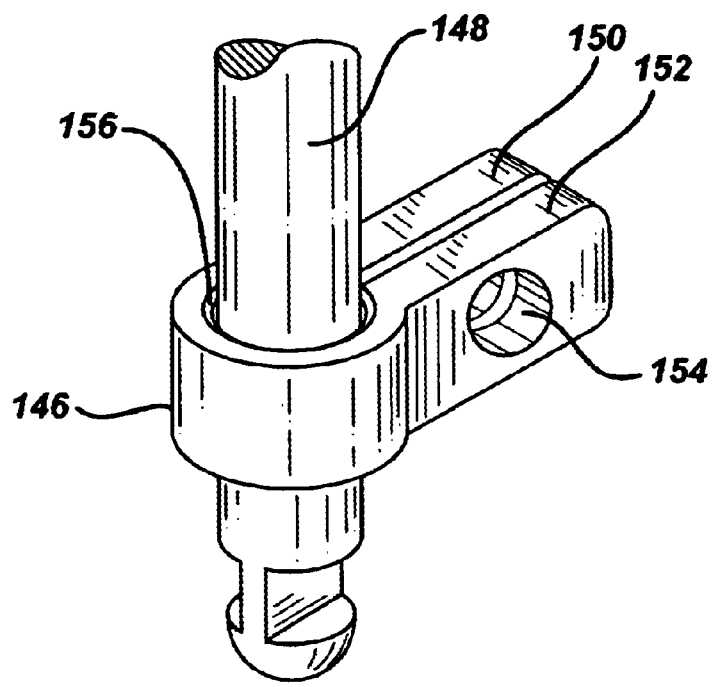
FIG. 9 illustrates a second spinal fixation coupling element and second spinal fixation element of FIG. 8.

An exemplary second spinal fixation coupling element 146 and second spinal fixation element 148 are further illustrated in FIG. 9. In this embodiment, second spinal fixation element 148 is a spinal fixation rod and second spinal fixation coupling element 146 is a slotted rod connector defining a rod receiving bore 156. Slotted rod connector 146 includes first and second tines 150, 152 through which a hole 154 is formed. Slotted rod connector 146 can be placed over post 124 using hole 154, then tightening of nut 144 will tighten slotted rod connector 146 both to T-coupler 120 and to second spinal fixation element 148, thus effecting a secure connection between a first, implanted spinal fixation element 30 and a second spinal fixation element 148. Further examples of rod connectors useful with the invention can be found in U.S. Pat. No. 4,648,388 to Steffee; U.S. Pat. No. 6,080,156 to Asher et al.; U.S. Pat. No. 5,474,551 to Finn et al.; and U.S. Pat. No. 5,810,816 to Roussouly et al.; each of which is incorporated herein by reference.

In one embodiment, the systems and methods described herein can be used to couple a first implanted spinal fixation element, for example, a VSP® Plate system available from DePuy AcroMed Inc. of Raynham Mass., to a known second spinal fixation element, such as an ISOL® Rod system also available from DePuy AcroMed Inc., while minimizing the amount of additional hardware to be stocked by the hospital or other healthcare organization where such systems are used. The second spinal fixation element can then be used to fix additional vertebrae according to the configuration and intended use of the second spinal fixation element using means understood by persons of ordinary skill in the art.

Using the system further described above, a method of the invention for extending a first, implanted spinal fixation element to one or more additional adjacent vertebrae while leaving the first, implanted spinal fixation element in place can include the steps of assembling a coupler having a connecting member and a head disposed on a distal end of the connecting member for holding the coupler to the first, implanted spinal fixation element; assembling a second spinal fixation element attachment member having a coupler attaching portion for attaching to the connecting member of the coupler and a second spinal fixation element attaching portion to the coupler; assembling a second spinal fixation element to the second spinal fixation element attachment member; and fixing the second spinal fixation element to the one or more additional adjacent vertebrae. Each of the steps in this method can be performed while the first, implanted spinal fixation element is left in place, and a person of ordinary skill in the art will recognize that the order of these steps may be varied in keeping with the spirit of the invention.

Where the first, implanted spinal fixation element is slotted and the head of the coupler is configured to hold the coupler to a slot on the first, implanted spinal fixation element, the head has a width shorter than a width of the slot in the first, implanted spinal fixation element, and a length longer than the width of the slot in the first, implanted spinal fixation element. The step of assembling the coupler to the first, implanted spinal fixation element can thus include placing the coupler in a first orientation wherein the head passes through the slot, passing the head through the slot, and placing the coupler in a second orientation wherein the head is trapped beneath the first, implanted spinal fixation element while the connecting member extends through the slot.

In addition, where the second spinal fixation element is a spinal fixation rod and the second spinal fixation element attaching portion of the second spinal fixation element attachment member defines a bore for accepting and attaching the spinal fixation rod, the step of assembling the second spinal fixation element to the to the second spinal fixation element attachment member includes fixing the rod within the bore.

A person of ordinary skill in the art will appreciate further features and advantages of the invention based on the above-described embodiments. Accordingly, the invention is not to be limited by what has been particularly shown and described, except as indicated by the appended claims. All publication and references cited herein are expressly incorporated herein by reference in their entity.

What is claimed is:

1. A coupler for connecting a first, slotted, implanted spinal fixation element to a second spinal fixation element, the coupler comprising:

a post and a head disposed on a distal end of the post, the head having a width shorter than a width of a slot in the first, slotted, implanted spinal fixation element and a length longer than the width of the slot in the first, slotted, implanted spinal fixation element, the post having a connecting element;

wherein when placed in a first orientation, the head passes through the slot in the first, slotted, implanted spinal fixation element, and when then placed in a second orientation, the head is trapped beneath the first, slotted, implanted spinal fixation element while the connecting element extends through the slot.

2. The coupler according to claim 1 wherein a proximal end of the post includes a driver element for connecting to a driver to rotate the coupler from the first orientation to the second orientation.

3. The coupler according to claim 1 wherein a proximal end of the post includes a visual indicator element indicating the rotational orientation of the coupler.

4. The coupler according to claim 1 wherein at opposed lengthwise ends, the head is radiused and beveled to facilitate rotation of the coupler.

5. The coupler according to claim 1 wherein a proximal face of the head includes surface features disposed thereon to increase friction between the coupler and the first, slotted, implanted spinal fixation element when the coupler is tightened thereto.

6. The coupler according to claim 1 wherein the connecting element comprises threads disposed on the post along a length thereof and a nut disposed on the threads for fixing the coupler to the first, slotted, implanted spinal fixation element after placement of the head in the second orientation.

7. The coupler according to claim 6 wherein the connecting element further comprises a beveled element having a bevel corresponding to a scallop provided on a proximal facing surface of the first, slotted, implanted spinal fixation element adjacent to the slot wherein upon tightening of the nut, the beveled element cooperates with the scallop to prevent relative movement of the coupler along a length of the slot.

8. A system for extending a first, implanted spinal fixation element to one or more additional adjacent vertebrae while leaving the first, implanted spinal fixation element in place, the system comprising:

a second spinal fixation element;

a coupler having a connecting member and a head disposed on a distal end of the connecting member for holding the coupler to a slot on the first, implanted spinal fixation element, the head having a width shorter than a width of the slot in the first, implanted spinal fixation element and a length longer than the width of the slot in the first, implanted spinal fixation element; and a second spinal fixation element attachment member having a coupler attaching portion for attaching to the connecting member of the coupler and a second spinal fixation element attaching portion;

wherein assembly of the coupler to the first, implanted spinal fixation element, the second spinal fixation element attachment member to the coupler, and the second spinal fixation element attachment member to the second spinal fixation element extends the first, implanted spinal fixation element to one or more adjacent vertebrae while leaving the first, implanted spinal fixation element in place.

9. The system according to claim 8 wherein a proximal end of the connecting member includes a driver element for connecting to a driver to rotate the coupler from the first orientation to the second orientation.

10. The system according to claim 8 wherein a proximal end of the connecting member includes a visual indicator element indicating the rotational orientation of the coupler.

11. The system according to claim 8 wherein at opposed lengthwise ends, the head is radiused and beveled to facilitate rotation of the coupler.

12. The system according to claim 8 wherein a proximal face of the head includes surface features disposed thereon to increase friction between the coupler and the first, implanted spinal fixation element when the coupler is tightened thereto.

13. The system according to claim 8 wherein the connecting member comprises a threaded post and a nut disposed on the threads for fixing the coupler to the first, implanted spinal fixation element after placement of the head in the second orientation.

14. The system according to claim 13 wherein the connecting member further comprises a beveled element having a bevel corresponding to a scallop provided on a proximal facing surface of the first, implanted spinal fixation element adjacent to the slot wherein upon tightening of the nut, the beveled element cooperates with the scallop to prevent relative movement of the coupler along a length of the slot.

15. The system according to claim 8 wherein the second spinal fixation element is a spinal fixation rod.

16. The system according to claim 15 wherein the second spinal fixation element attaching portion of the second spinal fixation element attachment member defines a bore for accepting and attaching the spinal fixation rod.

17. The system according to claim 16, wherein the connecting member comprises a threaded post and the coupler attaching portion of the second spinal fixation element attachment member defines a bore for accepting the threaded post and a nut for holding the second spinal fixation element attachment member to the connecting member.

18. A system for extending a first, implanted spinal fixation element to one or more additional adjacent vertebrae while leaving the first, implanted spinal fixation element in place, the system comprising:

a first, implanted spinal fixation element attached to a patient's spine and having a slot thereon;

a second spinal fixation element;

a coupler having a connecting member and a head disposed on a distal end of the connecting member for holding the coupler to the slot on the first, implanted spinal fixation element, the head having a width shorter than a width of the slot in the first, implanted spinal fixation element and a length longer than the width of the slot in the first, implanted spinal fixation element, wherein when placed in a first orientation, the head passes through the slot, and when then placed in a second orientation, the head is trapped beneath the first, implanted spinal fixation element while the connecting member extends through the slot; and a second spinal fixation element attachment member having a coupler attaching portion for attaching to the connecting member of the coupler and a second spinal fixation element attaching portion;

wherein assembly of the coupler to the slot on first, implanted spinal fixation element, the second spinal fixation element attachment member to the coupler, and the second spinal fixation element attachment member to the second spinal fixation element extends the first, implanted spinal fixation element to one or more adjacent vertebrae while leaving the first, implanted spinal fixation element in place.

19. The system according to claim 18 wherein the second spinal fixation element is a spinal fixation rod and the second spinal fixation element attaching portion of the second spinal fixation element attachment member defines a bore for accepting and attaching the spinal fixation rod.

20. A method for extending a first, implanted spinal fixation element to one or more additional adjacent vertebrae while leaving the first, implanted spinal fixation element in place, the method comprising:

providing a first, implanted spinal fixation element having a slot;

assembling a coupler having a connecting member and a head disposed on a distal end of the connecting member for holding the coupler to the slot on the first, implanted spinal fixation element, the head having a width shorter than a width of the slot in the first, implanted spinal fixation element and a length longer than the width of the slot in the first, implanted spinal fixation element;

assembling a second spinal fixation element attachment member having a coupler attaching portion for attaching to the connecting member of the coupler and a second spinal fixation element attaching portion to the coupler;

assembling a second spinal fixation element to the second spinal fixation element attachment member; and fixing the second spinal fixation element to the one or more additional adjacent vertebrae;

wherein the first, implanted spinal fixation element is left in place.

21. The method according to claim 20 wherein the step of assembling the coupler to the first, implanted spinal fixation element includes placing the coupler in a first orientation wherein the head passes through the slot, passing the head through the slot, and placing the coupler in a second orientation wherein the head is trapped beneath the first, implanted spinal fixation element while the connecting member extends through the slot.

22. The method according to claim 20 wherein the second spinal fixation element is a spinal fixation rod and the second spinal fixation element attaching portion of the second spinal fixation element attachment member defines a bore for accepting and attaching the spinal fixation rod;

the step of assembling the second spinal fixation element to the to the second spinal fixation element attachment member including fixing the rod within the bore.

* * * * *